（12）United States Patent
Robinson et al.

(10) Patent No.: US 9,256,126 B2
(45) Date of Patent: Feb. 9, 2016

(54) METHANOFULLERENES

(71) Applicants: Alex Philip Graham Robinson, Birmingham (GB); Jon Andrew Preece, Birmningham (GB); Richard Edward Palmer, Southbridge (GB); Andreas Frommhold, Anger (DE); Dongxu Yang, Birmingham (GB); Alexandra McClelland, Worcester (GB); Drew Athens, Dover, NH (US); Xiang Xu, Winchester, MA (US)

(72) Inventors: Alex Philip Graham Robinson, Birmingham (GB); Jon Andrew Preece, Birmningham (GB); Richard Edward Palmer, Southbridge (GB); Andreas Frommhold, Anger (DE); Dongxu Yang, Birmingham (GB); Alexandra McClelland, Worcester (GB); Drew Athens, Dover, NH (US); Xiang Xu, Winchester, MA (US)

(73) Assignee: IRRESISTIBLE MATERIALS LTD, Swansea, Wales (GB)

( * ) Notice: Subject to any disclaimer, the term of this patent is extended or adjusted under 35 U.S.C. 154(b) by 0 days.

(21) Appl. No.: 14/068,254

(22) Filed: Oct. 31, 2013

(65) Prior Publication Data
US 2014/0134843 A1  May 15, 2014

Related U.S. Application Data

(60) Provisional application No. 61/726,562, filed on Nov. 14, 2012.

(51) Int. Cl.
*G03F 7/038* (2006.01)
*G03F 7/027* (2006.01)
*C07C 69/96* (2006.01)
*G03F 7/20* (2006.01)
*G03F 7/38* (2006.01)
(Continued)

(52) U.S. Cl.
CPC .............. *G03F 7/027* (2013.01); *C07C 69/753* (2013.01); *C07C 69/96* (2013.01); *G03F 7/20* (2013.01); *G03F 7/38* (2013.01); *H01L 51/0047* (2013.01); *C07C 2104/00* (2013.01)

(58) Field of Classification Search
CPC ............. G03F 7/027; G03F 7/20; G03F 7/38; C07C 2104/00; H01L 51/0047
USPC ........... 430/270.1, 285.1, 322, 325, 913, 942, 430/296; 558/275
See application file for complete search history.

(56) References Cited

U.S. PATENT DOCUMENTS 6,117,617 A  9/2000  Kanayama
6,472,705 B1  10/2002  Bethune
(Continued)

FOREIGN PATENT DOCUMENTS

JP  2012177830 A  * 9/2012
JP  201 2201 61  * 10/2012
(Continued)

OTHER PUBLICATIONS
Oizuni etal, Japanese Journal of Applied Physics, 49, (2010) 06GF04-1 to 6.
(Continued)

*Primary Examiner* — Amanda C Walke
(74) *Attorney, Agent, or Firm* — The Patent Practice of Szmanda & Shelnut LLC (57) ABSTRACT

The present disclosure relates to novel methanofullerene derivatives, negative-type photoresist compositions prepared therefrom and methods of using them. The derivatives, their photoresist compositions and the methods are ideal for fine pattern processing using, for example, ultraviolet radiation, beyond extreme ultraviolet radiation, extreme ultraviolet radiation, X-rays and charged particle rays.

20 Claims, 2 Drawing Sheets

Pitch 44nm (22nm lines): 31.2 mJ/cm²

(51) Int. Cl.
*H01L 51/00* (2006.01)
*C07C 69/753* (2006.01)

(56) References Cited

U.S. PATENT DOCUMENTS

| | | |
|---|---|---|
| 6,503,688 B1 | 1/2003 | Preece |
| 6,750,471 B2 | 6/2004 | Bethune |
| 7,077,982 B2 | 7/2006 | Kinoshita |
| 7,388,771 B2 | 6/2008 | Ho |
| 7,456,421 B2 | 11/2008 | Lung |
| 7,463,512 B2 | 12/2008 | Lung |
| 7,514,367 B2 | 4/2009 | Lung |
| 7,527,985 B2 | 5/2009 | Lai |
| 7,534,647 B2 | 5/2009 | Lung |
| 7,586,778 B2 | 9/2009 | Ho |
| 7,605,079 B2 | 10/2009 | Lai |
| 7,616,472 B2 | 11/2009 | Lai |
| 7,619,237 B2 | 11/2009 | Lung |
| 7,642,539 B2 | 1/2010 | Lung |
| 7,670,749 B2 | 3/2010 | Palmer |
| 7,732,800 B2 | 6/2010 | Lai |
| 7,772,581 B2 | 8/2010 | Lung |
| 7,791,057 B2 | 9/2010 | Lung |
| 7,816,661 B2 | 10/2010 | Lai |
| 7,820,997 B2 | 10/2010 | Lai |
| 7,825,398 B2 | 11/2010 | Happ |
| 7,879,692 B2 | 2/2011 | Lung |
| 7,892,922 B2 | 2/2011 | Lee |
| 7,924,600 B2 | 4/2011 | Ho |
| 7,932,129 B2 | 4/2011 | Lung |
| 7,932,506 B2 | 4/2011 | Lung |
| 7,956,358 B2 | 6/2011 | Chen |
| 7,964,437 B2 | 6/2011 | Lung |
| 7,994,593 B2 | 8/2011 | Takulapalli |
| 8,034,546 B2 * | 10/2011 | Robinson et al. ............ 430/325 |
| 8,039,392 B2 | 10/2011 | Lai |
| 8,062,833 B2 | 11/2011 | Chen |
| 8,062,923 B2 | 11/2011 | Lung |
| 8,080,440 B2 | 12/2011 | Lai |
| 8,084,842 B2 | 12/2011 | Chen |
| 8,106,376 B2 | 1/2012 | Lai |
| 8,139,393 B2 | 3/2012 | Lai |
| 8,178,388 B2 | 5/2012 | Ho |
| 8,237,140 B2 | 8/2012 | Lung |
| 8,293,600 B2 | 10/2012 | Chen |
| 8,758,979 B2 * | 6/2014 | Robinson et al. ......... 430/270.1 |
| 2002/0139961 A1 | 10/2002 | Kinoshita |
| 2003/0011036 A1 | 1/2003 | Bethune |
| 2006/0102891 A1 | 5/2006 | Brabec |
| 2006/0119921 A1 | 6/2006 | Kinoshita |
| 2006/0284158 A1 | 12/2006 | Lung |
| 2006/0286743 A1 | 12/2006 | Lung |
| 2007/0131922 A1 | 6/2007 | Lung |
| 2007/0138458 A1 | 6/2007 | Lung |
| 2007/0154847 A1 | 7/2007 | Chen |
| 2007/0155172 A1 | 7/2007 | Lai |
| 2007/0176261 A1 | 8/2007 | Lung |
| 2007/0190447 A1 | 8/2007 | Ogata |
| 2007/0278529 A1 | 12/2007 | Lai |
| 2007/0281420 A1 | 12/2007 | Lai |
| 2007/0298328 A1 | 12/2007 | Palmer |
| 2008/0043520 A1 | 2/2008 | Chen |
| 2008/0061341 A1 | 3/2008 | Lung |
| 2008/0094873 A1 | 4/2008 | Lai |
| 2008/0094875 A1 | 4/2008 | Ho |
| 2008/0094885 A1 | 4/2008 | Ho |
| 2008/0096341 A1 | 4/2008 | Lai |
| 2008/0118874 A1 | 5/2008 | Robinson |
| 2008/0192534 A1 | 8/2008 | Lung |
| 2008/0197333 A1 | 8/2008 | Lung |
| 2008/0266940 A1 | 10/2008 | Lai |
| 2008/0285330 A1 | 11/2008 | Ho |
| 2009/0014757 A1 | 1/2009 | Takulapalli |
| 2009/0042335 A1 | 2/2009 | Lung |
| 2009/0101883 A1 | 4/2009 | Lai |
| 2009/0242880 A1 | 10/2009 | Chen |
| 2009/0251944 A1 | 10/2009 | Happ |
| 2009/0255585 A1 | 10/2009 | Shaikh |
| 2009/0261313 A1 | 10/2009 | Lung |
| 2009/0303774 A1 | 12/2009 | Ho |
| 2010/0019215 A1 | 1/2010 | Lung |
| 2010/0019221 A1 | 1/2010 | Lung |
| 2010/0019230 A1 | 1/2010 | Lee |
| 2010/0029062 A1 | 2/2010 | Lung |
| 2010/0039846 A1 | 2/2010 | Lai |
| 2010/0068878 A1 | 3/2010 | Lung |
| 2010/0163103 A1 * | 7/2010 | Wang et al. ................... 136/256 |
| 2010/0186798 A1 | 7/2010 | Tormen |
| 2010/0207095 A1 | 8/2010 | Lai |
| 2010/0221888 A1 | 9/2010 | Ho |
| 2010/0261329 A1 | 10/2010 | Lung |
| 2011/0012084 A1 | 1/2011 | Lai |
| 2011/0195362 A1 * | 8/2011 | Watanabe et al. ............. 430/323 |
| 2012/0037915 A1 | 2/2012 | Kugler |
| 2012/0055236 A1 | 3/2012 | Takulapalli |
| 2012/0077309 A1 | 3/2012 | Chen |
| 2012/0251953 A1 | 10/2012 | Robinson |
| 2012/0326201 A1 | 12/2012 | Ohnuma |
| 2013/0202999 A1 | 8/2013 | Iwato |

FOREIGN PATENT DOCUMENTS

| | | |
|---|---|---|
| WO | WO/00/36469 A1 | 6/2000 |
| WO | WO/2006/030234 A2 | 3/2006 |
| WO | WO/2006/030239 A2 | 3/2006 |
| WO | WO/2006/030240 A2 | 3/2006 |

OTHER PUBLICATIONS

Oizuni etal, Adv in Resist Materials and Processes Technology XXVIII, SPIE vol. 7972 (2011) 797209-1 to 7.

Tetsuya Tada etal, Microelectronic Eng. 61-62 (2002) 734-743.

* cited by examiner

Figure 1 Pitch 44nm (22nm lines): 31.2 mJ/cm$^2$

Figure 2 Pitch 36nm (18 nm lines): 21.2mJ/cm$^2$

Figure 3: Pitch 50 (25nm lines): 48mJ/cm$^2$

Figure 4: line dosage of 575 pC/cm

Figure 5: line dosage of 575 pC/cm

Figure 6 line dosage of 600 pC/cm

METHANOFULLERENES

FIELD OF INVENTION

The present invention relates to novel methanofullerene derivatives, negative-type photoresist compositions prepared therefrom and methods of using them. The derivatives, their photoresist compositions and the methods are ideal for fine pattern processing using, for example, ultraviolet radiation, extreme ultraviolet radiation, beyond extreme ultraviolet radiation, X-rays and charged particle rays.

BACKGROUND

As is well known, the manufacturing process of various kinds of electronic or semiconductor devices such as ICs, LSIs and the like involves a fine patterning of a resist layer on the surface of a substrate material such as a semiconductor silicon wafer. This fine patterning process has traditionally been conducted by the photolithographic method in which the substrate surface is uniformly coated with a positive or negative tone photoresist composition to form a thin layer of the photoresist composition and selectively irradiating with actinic rays (such as ultraviolet light) through a photomask followed by a development treatment to selectively dissolve away the photoresist layer in the areas exposed or unexposed, respectively, to the actinic rays leaving a patterned resist layer on the substrate surface. The thus obtained patterned resist layer is utilized as a mask in the subsequent treatment on the substrate surface such as etching. The fabrication of structures with dimensions of the order of nanometers is an area of considerable interest since it enables the realization of electronic and optical devices which exploit novel phenomena such as quantum confinement effects and also allows greater component packing density. As a result, the resist layer is required to have an ever increasing fineness which can by accomplished only by using actinic rays having a shorter wavelength than the conventional ultraviolet light. Accordingly, it is now the case that, in place of the conventional ultraviolet light, electron beams (e-beams), excimer laser beams, EUV, BEUV and X-rays are used as the short wavelength actinic rays. Needless to say the minimum size obtainable is primarily determined by the performance of the resist material and the wavelength of the actinic rays. Various materials have been proposed as suitable resist materials. In the case of negative tone resists based on polymer crosslinking, there is an inherent resolution limit of about 10 nm, which is the approximate radius of a single polymer molecule.

It is also known to apply a technique called "chemical amplification" to the polymeric resist materials. A chemically amplified resist material is generally a multi-component formulation in which there is a main polymeric component, such as a novolac resin which contributes towards properties such as resistance of the material to etching and its mechanical stability and one or more additional components which impart desired properties to the resist and a sensitizer. By definition, the chemical amplification occurs through a catalytic process involving the sensitizer which results in a single irradiation event causing exposure of multiple resist molecules. In a typical example the resist comprises a polymer and a photoacid generator (PAG) as sensitizer. The PAG releases a proton in the presence of radiation (light or e-beam). This proton then reacts with the polymer to cause it to lose a functional group. In the process, a second proton is generated which can then react with a further molecule. The speed of the reaction can be controlled, for example, by heating the resist film to drive the reaction. After heating, the reacted polymer molecules are free to react with remaining components of the formulation, as would be suitable for a negative-tone resist. In this way the sensitivity of the material to actinic radiation is greatly increased, as small numbers of irradiation events give rise to a large number of exposure events.

In such chemical amplification schemes, irradiation results in cross-linking of the exposed resist material; thereby creating a negative tone resist. The polymeric resist material may be self cross-linking or a cross linking molecule may be included. Chemical amplification of polymeric-based resists is disclosed in U.S. Pat. Nos. 5,968,712, 5,529,885, 5,981,139 and 6,607,870.

Various methanofullerene derivatives have been shown to be useful e-beam resist materials by the present inventors, Appl. Phys. Lett. volume 72, page 1302 (1998), Appl. Phys. Lett. volume 312, page 469 (1999), Mat. Res. Soc. Symp. Proc. volume 546, pace 219 (1999) and U.S. Pat. No. 6,117,617.

As can be seen there is an ongoing desire to obtain finer and finer resolution of photoresists that will allow for the manufacture of smaller and smaller semiconductor devices in order to meet the requirements of current and further needs. It is also desirable to create materials which can be used in conjunction with these photoresists which will be more robust to the processes used to create current semiconductor devices, such as, for example, etching resistance.

SUMMARY OF THE DISCLOSURE

In a first embodiment, a methanofullerene comprising the general formula:

is disclosed wherein C2x represents a fullerene with x at least 10, y is 1-6, n is 0-1, alkyl is a branched or unbranched, substituted or unsubstituted divalent alkyl chain of 1-16 carbons with or without one or more heteroatoms substituted into the chain, aryl is a substituted or unsubstituted divalent phenyl group, heteroaromatic group, or fused aromatic or fused heteroaromatic group, and R is H or an acid labile group. An example of a disclosed methanofullerene comprises the general formula:

In a second embodiment, the methanofullerene of the above embodiment includes divalent alkyl groups comprising a substituted or unsubstituted methylene, ethylene or 1,3-propylene group, and the divalent aryl group comprises a substituted or unsubstituted phenylene group.

In a third embodiment, the methanofullerene of all the above embodiments includes R as either H or an acid labile alkoxycarbonyl group.

In a fourth embodiment, the methanofullerene of the above embodiments includes divalent alkyl group wherein the heteroatoms are one or more of oxygen, nitrogen, sulfur, or oxides of sulfur and/or the alkyl chains may be substituted with fluorine atoms.

In a fifth embodiment, a negative-tone photoresist composition is disclosed comprising at least one of any of the methanofullerenes of the above embodiments, at least one photo acid generator, at least one crosslinker, and at least one solvent, wherein the crosslinker crosslinks at least with the methanofullerene when processed.

In a sixth embodiment, the negative-tone photoresist composition of the above embodiments is disclosed wherein the at least one photoacid generator comprises an onium salt compound, a sulfone imide compound, a halogen-containing compound, a sulfone compound, a sulfonate ester compound, a quinine-diazide compound, or a diazomethane compound.

In a seventh embodiment, the negative-tone photoresist composition of any of the above embodiments is disclosed contain a novolac, a poly-hydroxystyrene, a polyacrylate, or a maleic anhydride ester-acid polymer crosslinking additive.

In an eighth embodiment, the negative-tone photoresist composition of any of the above embodiments is disclosed wherein the at least one crosslinker comprises an acid sensitive monomer or polymer.

In a ninth embodiment, the negative-tone photoresist composition of any of the above embodiments is disclosed wherein at least one methanofullerene comprising the general formula is also included:

wherein x is at least 10, y is 1-6, a is 1-10 and R is H or an acid labile group and the —CH$_2$—CH$_2$— group may be substituted with fluorine atoms. An example of a disclosed methanofullerene comprises the general formula:

In a further embodiment, a process for using any of the above mentioned negative-tone compositions is disclosed including the steps of obtaining a substrate, applying any one of the photoresist compositions of the above embodiments to a desired wet thickness, optionally heating the coated substrate to remove a majority of the solvent to obtain a desired thickness, imagewise exposing the coating to actinic radiation, removing the unexposed areas of the coating, and optionally heating the remaining coating.

In still a further embodiment, the process of the above embodiment is disclosed including a further step of either heating the imagewise exposed coating prior to removing the unexposed areas of the coating or exposing the coating to infrared exposure.

In still a further embodiment, the process of the above embodiment is disclosed wherein the unexposed areas are removed by treating with an organic solvent composition.

In still a further embodiment, the process of the above embodiment is disclosed wherein the actinic radiation is ultraviolet, extreme ultraviolet, beyond extreme ultraviolet, charged particle beam or electron beam.

In all the above embodiments, the fullerene may be substituted with more than one type of methanofullerene.

DETAILED DESCRIPTION

As used herein, the conjunction "and" is intended to be inclusive and the conjunction "or" is not intended to be exclusive unless otherwise indicated. For example, the phrase "or, alternatively" is intended to be exclusive.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The methanofullerene of the current application for patent is of general formulation:

x is at least 10, such as, for example, 10, 25, 30, 35, 38, 39, 41, 42, 45 and 48 wherein the example fullerene core is C$_{20}$, C$_{50}$, C$_{60}$, C$_{70}$, C$_{76}$, C$_{78}$, C$_{82}$, C$_{84}$, C$_{90}$ and C$_{96}$. y is between about 1 to about 6 representing the number of methano substituents on the fullerene. As is well known in the industry, manufacture of such materials often results in mixtures of the number of substitutions such that a useful material may have, for example, y=2.35 or 5.1 representing an average of a mixture of substitutions. Thus y is not meant to be an absolute number of substituents but an average thereof. An example of a disclosed methanofullerene comprises the general formula:

The alkyl group can be a branched or unbranched divalent alkyl chain of 1-16 carbons with or without heteroatoms substituted into the chain, such as, for example, —$CH_2$—, —$CH_2CH_2$—, —$CH(CH_3)CH_2$—, —$CH_2CH_2CH_2$—, —$CH_2CH_2CH_2CH_2$—, butylene isomers, and the higher analogs up to and including hexadecylene, as well as their isomers. As used herein alkyl also includes any unsaturations in the chain such an olefin group, such as for example, —CH=CH—, or an alkynyl group. As mentioned the alkyl group may have heteroatoms substituted into the chain as part or the chain, such as O, N, S, S=O or $SO_2$ and the like, such as, for example, —$(CH_2CH_2$—$O)_z$— wherein z is between about 1 and about 16, or —$(CH_2CH_2NH)_w$— wherein w is between about 1 and about 16, and the like. Also included are branched alkyl groups that contain heteroatoms in the ring, such as, for example —$(CH_2CH_2NR'')_y$— wherein R" can be a branched or unbranched divalent alkyl chain of 1-16 carbons with or without heteroatoms substituted into the R" chain.

Aryl is a substituted or unsubstituted divalent aromatic group, such aromatic groups include, for example the phenylenes (—$C_6H_4$—), the fused divalent aromatic group, such as, for example, the naphthylenes (—$C_{10}H_6$—), the anthacenylenes (—$C_{14}H_8$—) and the like, as well as the heteroaromatic groups, such as, for example, the nitrogen heterocycles: pyridines, quinolines, pyrroles, indoles, pyrazoles, the triazines, and other nitrogen-containing aromatic heterocycles well known in the arts, as well as the oxygen heterocycles: furans, oxazoles and other oxygen-containing aromatic heterocycles, as well the sulfur containing aromatic heterocycles, such as, for example, thiophenes.

R may be H or D or an acid labile group, including, for example, substituted methyl groups, 1-substituted ethyl groups, 1-substituted alkyl groups, silyl groups, germyl groups, alkoxycarbonyl group, acyl groups and cyclic acid-dissociable groups. The substituted methyl groups include, for example, the methoxymethyl group, methylthiomethyl group, ethoxy methyl group, ethylthiomethyl group, methoxyethoxy methyl group, benzyloxymethyl group, benzylthiomethyl group, phenacyl group, bromophenacyl group, methoxyphenacyl group, methylthiophenacyl group, α-methylphenacyl group, cyclopropylmethyl group, benzyl group, diphenyl methyl group, triphenylmethyl group, bromobenzyl group, nitrobenzyl group, methoxybenzyl group, methylthiobenzyl group, ethoxy benzyl group, ethylthiobenzyl group, piperonyl group, methoxycarbonylmethyl group, ethoxy carbonylmethyl group, N-propoxy carbonylmethyl group, isopropoxy carbonylmethyl group, N-butoxycarbonylmethyl group and t-butoxycarbonylmethyl group. The 1-substituted ethyl groups include, for example. 1-methoxyethyl group, 1-methylthioethyl group, 1,1-dimethoxyethyl group, 1-ethoxy ethyl group, 1-ethylthioethyl group, 1,1-diethoxy ethyl group, 1-phenoxyethyl group, 1-phenylthioethyl group, 1,1-diphenoxyethyl group, 1-benzyloxyethyl group, 1-benzylthioethyl group, 1-cyclopropylethyl group, 1-phenylethyl group, 1,1-diphenyl ethyl group, 1-methoxycarbonylethyl group, 1-ethoxy carbonylethyl group, 1-N-propoxy carbonylethyl group, 1-isopropoxy carbonylethyl group, 1-N-butoxycarbonylethyl group and the 1-t-butoxycarbonylethyl group. The 1-substituted alkyl group include the isopropyl group, sec-butyl group, t-butyl group, 1,1-dimethylpropyl group, 1-methylbutyl group and 1,1-dimethylbutyl group.

The silyl acid labile groups include, for example, the trimethyl silyl group, ethyldimethylsilyl group, methyldiethylsilyl group, triethylsilyl group, isopropyldimethylsilyl group, methyldiisopropylsilyl group, triisopropylsilyl group, t-butyldimethylsilyl group, methyldi-t-butylsilyl group, tri-t-butylsilyl group, phenyldimethylsilyl group, methyldiphenyl silyl group and triphenylsilyl group. The germyl groups include, for example, the trimethyl germyl group, ethyldimethylgermyl group, methyldiethylgermyl group, triethylgermyl group, isopropyldimethylgermyl group, methyldiisopropylgermyl group, triisopropylgermyl group, t-butyldimethylgermyl group, methyldi-t-butylgermyl group, tri-t-butylgermyl group, phenyldimethylgermyl group, methyldiphenyl germyl group and triphenylgermyl group.

The alkoxycarbonyl acid labile groups include the methoxycarbonyl group, ethoxy carbonyl group, isopropoxy carbonyl group and t-butoxycarbonyl group. The acyl acid labile groups include, for example, the acetyl group, propionyl group, butyryl group, heptanoyl group, hexanoyl group, valeryl group, pivaloyl group, isovaleryl group, lauroyl group, myristoyl group, palmitoyl group, stearoyl group, oxaryl group, malonyl group, succinyl group, glutaryl group, adipoyl group, piperoyl group, suberoyl group, azelaoyl group, sebacoyl group, acrylyl group, propioloyl group, methacryloyl group, crotonoyl group, oleoyl group, maleoyl group, fumaroyl group, mesaconoyl group, camphoroyl group, benzoyl group, phthaloyl group, isophthaloyl group, terephthaloyl group, naphthoyl group, toluoyl group, hydroatropoyl group, atropoyl group, cinnamoyl group, furoyl group, thenoyl group, nicotinoyl group, isonicotinoyl group, p-toluene sulfonyl group and the mesyl group.

Cyclic acid groups include, for example, the cyclopropyl group, cyclopentyl group, cyclohexyl group, cyclohexanyl group, 4-methoxycyclohexyl group, tetrahydropyranyl group, tetrahydrofuranyl group, tetrahydrothiopyranyl group, tetrahydrothiofuranyl group, 3-bromo tetrahydropyranyl group, 4-methoxy tetrahydropyranyl group, 4-methoxy tetrahydrothiopyranyl group and 3-tetrahydrothiophene-1,1-dioxy group.

In the above structure n may be 0 or 1. In the case where n=1, the methanofullerene contains a benzyl alcohol which will crosslink with the crosslinkers when processed. Additionally, in a further embodiment, when the benzyl alcohol is protected with the acid labile groups of the current disclosure, a reactive benzyl alcohol will be obtained when deprotected and, as above, will crosslink with the crosslinkers when processed.

The fullerenes may also be substituted with other groups that introduce certain desired characteristics to the fullerene such as, for example, solubility in certain solvents or compatibility with certain components of the formulation. The fullerenes can be prepared by any of a number of methods, such as, for example, the procedure as shown in the examples below.

The photo acid generators (PAGs) suitable for the negative-tone photoresist of the current disclosure include onium salt compounds, sulfone imide compounds, halogen-containing compounds, sulfone compounds, ester sulfonate compounds, quinone diazide compounds, and diazomethane compounds. Specific examples of these acid generators are indicated below.

Examples of onium salt compounds include sulfonium salts, iodonium salts, phosphonium salts, diazonium salts and pyridinium salts. Specific examples of onium salt compounds include diphenyl(4-phenylthiophenyl)sulphonium hexafluoroantimonate, 4,4'-bis[diphenylsulfoniolphenylsulphide bis hexafluoroantimonate and combinations there of, triphenylsulfonium nonafluorobutanesulfonate, triphenylsulfonium trifluoromethanesulfonate, triphenylsulfonium pyrenesulfonate, triphenylsulfonium dodecylbenzenesulfonate, triphenylsulfonium p-toluene sulfonate, triphenylsulfonium benzenesulfonate, triphenylsulfonium 10-camphor-sulfonate, triphenylsulfonium octanesulfonate, triphenylsulfonium 2-trifluoromethyl benzenesulfonate, triphenylsulfonium hexafluoroantimonate, triarylsulfonium hexafluoroantimonates, the triarylsulfonium hexafluorophosphates, the triarylsulfonium tetrafluoroborates as well as other tetrafluoroborates, triphenylsulfonium napthalenesulfonate, tri(4-hydroxyphenyl)sulfonium nonafluorobutanesulfonate, tri(4-hydroxyphenyl)sulfoniumtrifluoromethanesulfonate, tri(4-hydroxyphenyl)sulfonium pyrenesulfonate, tri(4-hydroxyphenyl) sulfoniumdodecylbenzenesulfonate, tri(4-hydroxyphenyl)sulfonium p-toluene sulfonate, tri(4-hydroxyphenyl)sulfonium benzenesulfonate, tri(4-hydroxyphenyl)sulfonium10-camphor-sulfonate, tri(4-hydroxyphenyl)sulfonium octanesulfonate, tri(4-hydroxyphenyl)sulfonium 2-trifluoromethylbenzenesulfonate, tri(4-hydroxyphenyl)sulfonium hexafluoroantimonate, tri(4-hydroxyphenyl)sulfonium napthalenesulfonate, diphenyliodonium nonafluorobutanesulfonate, diphenyliodonium trifluoromethanesulfonate, diphenyliodonium pyrenesulfonate, diphenyliodonium dodecylbenzenesulfonate, diphenyliodonium p-toluene sulfonate, diphenyliodonium benzenesulfonate, diphenyliodonium 10-camphorsulfonate, diphenyliodonium octanesulfonate, diphenyliodonium 2-trifluoromethylbenzenesulfonate, bis(4-t-butylphenyl)iodonium nonafluorobutanesulfonate, bis(4-t-butylphenyl)iodonium trifluoromethanesulfonate, bis(4-t-butylphenyl) iodonium pyrenesulfonate, bis(4-t-butylphenyl)iodonium dodecylbenzenesulfonate, bis(4-t-butylphenyl)iodonium p-toluene sulfonate, bis(4-t-butylphenyl)iodonium benzenesulfonate, bis(4-t-butylphenyl)iodonium 10-camphor-sulfonate, bis(4-t-butylphenyl)iodonium octanesulfonate, bis(4-t-butylphenyl) iodonium 2-trifluoromethylbenzenesulfonate, 4-hydroxy-1-naphthyl tetrahydrothiophenium trifluoromethanesulfonate and 4,7-dihydroxy-1-naphthyl tetrahydrothiophenium trifluoromethanesulfonate.

Specific examples of a sulfone imide compound include N-(trifluoromethylsulfonyloxy)succinimide, N-(trifluoromethylsulfonyloxy)phthalimide, N-(trifluoromethylsulfonyloxy)diphenylmaleimide, N-(trifluoromethylsulfonyloxy)bicyclo[2.2.1]hepto-5-ene-2,3-dicarboxyimide, N-(trifluoromethylsulfonyloxy)-7-oxabicyclo[2.2.1]hepto-5-ene-2,3-dicarboxyimide, N-(trifluoromethylsulfonyloxy) bicyclo[2.2.1]heptane-5,6-oxy-2,3-dicarboxyimide, N-(trifluoromethylsulfonyloxy)naphthylimide, N-(10-camphorsulfonyloxy)succinimide, N-(10-camphor-sulfonyloxy) phthalimide, N-(10-camphor-sulfonyloxy)diphenyl maleimide, N-(10-camphor-sulfonyloxy)bicyclo[2.2.1] hepto-5-ene-2,3-dicarboxyimide, N-(10-camphor-sulfonyloxy)-7-oxabicyclo[2.2.1]hepto-5-ene-2,3-dicarboxyimide, N-(10-camphor-sulfonyloxy)bicyclo[2.2.1]heptane-5,6-oxy-2,3-dicarboxyimide, N-(10-camphor-sulfonyloxy)naphthylimide, N-(p-toluene sulfonyloxy)succinimide, N-(p-toluene sulfonyloxy)phthalimide, N-(p-toluene sulfonyloxy) diphenyl maleimide, N-(p-toluene sulfonyloxy)bicyclo [2.2.1]hepto-5-ene-2,3-dicarboxyimide, N-(p-toluene sulfonyloxy)-7-oxabicyclo[2.2.1]hepto-5-ene-2,3-dicarboxyimide, N-(p-toluene sulfonyloxy)bicyclo[2.2.1]heptane-5,6-oxy-2,3-dicarboxyimide, N-(p-toluene sulfonyloxy)naphthylimide, N-(2-trifluoromethylbenzenesulfonyloxy)succinimide, N-(2-trifluoromethylbenzenesulfonyloxy) phthalimide, N-(2-trifluoromethylbenzenesulfonyloxy) diphenyl maleimide, N-(2-trifluoromethylbenzenesulfonyloxy)bicyclo[2.2.1]hepto-5-ene-2,3-dicarboxyimide, N-(2-trifluoromethylbenzenesulfonyloxy)-7-oxabicyclo[2.2.1] hepto-5-ene-2,3-dicarboxyimide, N-(2-trifluoromethylbenzenesulfonyloxy) bicyclo[2.2.1]heptane-5,6-oxy-2,3-dicarboxyimide, N-(2-trifluoromethylbenzenesulfonyloxy) naphthylimide, N-(4-fluorobenzenesulfonyloxy)succinimide, N-(4-fluorobenzenesulfonyloxy)phthalimide, N-(4-fluorobenzenesulfonyloxy)diphenyl maleimide, N-(4-fluorobenzenesulfonyloxy)bicyclo[2.2.1]hepto-5-ene-2,3-dicarboxyimide, N-(4-fluorobenzenesulfonyloxy)-7-oxabicyclo[2.2.1]hepto-5-ene-2,3-dicarboxyimide, N-(4-fluorobenzenesulfonyloxy)bicyclo[2.2.1]heptane-5,6-oxy-2,3-dicarboxyimide, N-(4-fluorobenzenesulfonyloxy) naphthylimide, N-(nonafluorobutylsulfonyloxy) succinimide, N-(nonafluorobutylsulfonyloxy)phthalimide, N-(nonafluorobutylsulfonyloxy)diphenyl maleimide, N-(nonafluorobutylsulfonyloxy)bicyclo[2.2.1]hepto-5-ene-2,3-dicarboxyimide, N-(nonafluorobutylsulfonyloxy)-7-oxabicyclo[2.2.1]hepto-5-ene-2,3-dicarboxyimide, N-(nonafluorobutylsulfonyloxy) bicyclo[2.2.1]heptane-5 6-oxy-2,3-dicarboxyimide and N-(nonafluorobutylsulfonyloxy) naphthylimide.

Examples of halogen-containing compounds include, for example, haloalkyl group-containing hydrocarbon compounds and haloalkyl group-containing heterocyclic compounds. Specific examples of halogen-containing compounds include (poly)trichloromethyl-s-triadine derivatives such as phenyl-bis(trichloromethyl)-s-triadine, 4-methoxyphenyl-bis(trichloromethyl)-s-triadine and 1-naphthyl-bis (trichloromethyl)-s-triadine, and 1,1-bis(4-chlorophenyl)-2, 2,2-trichloroethane.

Examples of sulfone compounds include, for example, β-ketosulfone and β-sulfonylsulfone, and the α-diazo compounds thereof. Specific examples of the sulfone compounds include phenacyl phenylsulfone, mesitylphenacyl sulfone, bis(phenylsulfonyl)methane, 1,1-bis(phenylsulfonyl)cyclobutane, 1,1-bis(phenylsulfonyl)cyclopentane, 1,1-bis (phenylsulfonyl)cyclo hexane, and 4-trisphenacyl sulfone.

Examples of sulfonate ester compounds include alkylsulfonate esters, haloalkyl sulfonate esters, aryl sulfonate esters sand imino sulfonates. Specific examples of sulfonate ester compounds include benzoin tosylate, pyrogallol tristrifluoromethanesulfonate, pyrogallol trisnonafluorobutanesulfonate, pyrogallol methanesulfonate triester, nitrobenzyl-9,10-diethoxy anthracene-2-sulfonate, α-methylol benzoin tosylate, α-methylol benzoin octanesulfonate, α-methylol benzoin trifluoromethanesulfonate and α-methylol benzoin dodecylsulfonate.

Examples of quinine diazide compounds include compounds containing a 1,2-quinone diazide sulfonyl group such as the 1,2-benzoquinone diazide-4-sulfonyl group, 1,2-naphthoquinone diazide-4-sulfonyl group, 1,2-naphtho quinine diazide-5-sulfonyl group and 1,2-naphthoquinone diazide-6-sulfonyl group. Specific examples of quinone diazide compounds include 1,2-quinone diazidesulfonate esters of (poly)

hydroxyphenylaryl ketones such as 2,3,4-trihydroxybenzophenone, 2,4,6-trihydroxybenzophenone, 2,3,4,4'-tetrahydroxybenzophenone, 2,2',3,4-tetrahydroxybenzophenone, 3'-methoxy-2,3,4,4'-tetrahydroxybenzophenone, 2,2',4,4'-tetrahydroxybenzophenone, 2,2'3,4,4'-pentahydroxybenzophenone, 2,2'3,4,6'-pentahydroxybenzophenone, 2,3,3'4,4',5'-hexahydroxybenzophenone, 2,3'4,4',5',6-hexahydroxybenzophenone; 1,2-quinone diazide sulfonate esters of bis[(poly)hydroxyphenyl]alkanes such as bis(4-hydroxyphenyl)methane, bis(2,4-dihydroxyphenyl)methane, bis(2,3,4-trihydroxyphenyl)methane, 2,2-bis(4-hydroxyphenyl)propane, 2,2-bis(2,4-dihydroxyphenyl)propane and 2,2-bis(2,3,4-trihydroxyphenyl)propane; 1,2-quinone diazide sulfonate esters of (poly)hydroxytriphenylalkanes such as 4,4'-dihydroxytriphenylmethane, 4,4',4"-trihydroxytriphenylmethane, 2,2',5,5'-tetramethyl-2",4,4'-trihydroxytriphenylmethane, 3,3',5,5'-tetramethyl-2",4,4'-trihydroxytriphenylmethane, 4,4',5,5'-tetramethyl-2,2',2"-trihydroxytriphenylmethane, 2,2',5,5'-tetramethyl-4,4',4"-trihydroxytriphenylmethane, 1,1,1-tris(4-hydroxyphenyl)ethane, 1,1-bis(4-hydroxyphenyl)-1-phenylethane, 1,1-bis(4-hydroxyphenyl)-1-[4-{1-(4-hydroxyphenyl)-1-methylethyl}phenyl ethane, 1,1,3-tris(2,5-dimethyl-4-hydroxyphenyl)propane, 1,1,3-tris(2,5-dimethyl-4-hydroxyphenyl)butane and 1,3 3-tris(2,5-dimethyl-4-hydroxyphenyl)butane; and 1,2-quinone diazide sulfonate esters of (poly)hydroxyphenylflavans such as 2,4,4-trimethyl-2',4',7-trihydroxy-2-phenylflavan and 2,4,4-trimethyl-2',4',5',6',7-pentahydroxy-2-phenylflavan.

Specific examples of diazomethane compounds include bis(trifluoromethylsulfonyl)diazomethane, bis(cyclohexylsulfonyl)diazomethane, bis(phenylsulfonyl)diazomethane, bis(p-toluene sulfonyl)diazomethane, methylsulfonyl-p-toluene sulfonyldiazomethane, 1-cyclohexylsulfonyl-1-(1,1-dimethylethylsulfonyl)diazomethane and bis(1,1-dimethylethylsulfonyl)diazomethane.

The compositions of the current disclosure may contain one or more of the above mentioned photoacid generators.

Crosslinkers suitable for the current disclosure constitute compounds able to cross-link with the methanofullerene during the process such that when the methanofullerene is substituted with a phenol or similar group, such as, for example, an alkyl —OH group, or when the methanofullerene is deprotected to provide for a phenol or similar group, the crosslinker will react with the —OH group situated on the phenol or similar group. Not to be held to theory, it is believed that the acid that is generated by exposure to the actinic radiation not only reacts with the acid-labile group of the methanofullerene but aids in the reaction of the crosslinker with itself and with the methanofullerene. Examples of crosslinkers include compounds comprising at least one type of substituted group that possess a cross-linking reactivity with the phenol or similar group of the methanofullerene. Specific examples of this crosslinking group include the glycidyl ether group, glycidyl ester group, glycidyl amino group, methoxymethyl group, ethoxy methyl group, benzyloxymethyl group, dimethylamino methyl group, diethylamino methyl group, dimethylol amino methyl group, diethylol amino methyl group, morpholino methyl group, acetoxymethyl group, benzyloxy methyl group, formyl group, acetyl group, vinyl group and isopropenyl group.

Examples of compounds having the aforementioned cross-linking substituted group include, for example, bisphenol A-based epoxy compounds, bisphenol F-based epoxy compounds, bisphenol S-based epoxy compounds, novolac resin-based epoxy compound, resol resin-based epoxy compounds, poly(hydroxystyrene)-based epoxy compounds, methylol group-containing melamine compounds, methylol group-containing benzoguanamine compounds, methylol group-containing urea compounds, methylol group-containing phenol compounds, alkoxyalkyl group-containing melamine compounds, alkoxyalkyl group-containing benzoguanamine compounds, alkoxyalkyl group-containing urea compounds, alkoxyalkyl group-containing phenol compounds, carboxymethyl group-containing melamine resins, carboxy methyl group-containing benzoguanamine resins, carboxymethyl group-containing urea resins, carboxymethyl group-containing phenol resins, carboxymethyl group-containing melamine compounds, carboxymethyl group-containing benzoguanamine compounds, carboxymethyl group-containing urea compounds, and carboxymethyl group-containing phenol compounds, methylol group-containing phenol compounds, methoxymethyl group-containing melamine compounds, methoxymethyl group-containing phenol compounds, methoxymethyl group-containing glycol-uril compounds, methoxymethyl group-containing urea compounds and acetoxymethyl group-containing phenol compounds. The methoxymethyl group-containing melamine compounds are commercially available as, for example, CYMEL300, CYMEL301, CYMEL303, CYMEL305 (manufactured by Mitsui Cyanamid), the methoxymethyl group-containing glycol-uril compounds are commercially available as, for example, CYMEL117 4 (manufactured by Mitsui Cyanamid), and the methoxymethyl group-containing urea compounds are commercially available as, for example, MX290 (manufactured by Sanwa Chemicals).

Examples of suitable solvents for the current disclosure include ethers, esters, etheresters, ketones and ketoneesters and, more specifically, ethylene glycol monoalkyl ethers, diethylene glycol dialkyl ethers, propylene glycol monoalkyl ethers, propylene glycol dialkyl ethers, acetate esters, hydroxyacetate esters, lactate esters, ethylene glycol monoalkylether acetates, propylene glycol monoalkylether acetates, alkoxyacetate esters, (non-)cyclic ketones, acetoacetate esters, pyruvate esters and propionate esters. Specific examples of these solvents include ethylene glycol monomethyl ether, ethylene glycol monoethyl ether, ethylene glycol monopropyl ether, ethylene glycol monobutyl ether, diethylene glycol dimethyl ether, diethylene glycol diethyl ether, diethylene glycol dipropyl ether, diethylene glycol dibutyl ether, methylcellosolve acetate, ethyl cellosolve acetate, propylene glycol monomethyletheracetate, propylene glycol monoethyletheracetate, propylene glycol monopropyletheracetate, isopropenyl acetate, isopropenyl propionate, methylethyl ketone, cyclohexanone, 2-heptanone, 3-heptanone, 4-heptanone, 2-hydroxypropionate ethyl, 2-hydroxy-2-methylpropionate ethyl, ethoxy acetate ethyl, hydroxyacetate ethyl, 2-hydroxy-3-methyl methylbutyrate, 3-methoxybutylacetate, 3-methyl-3-methoxybutylacetate, 3-methyl-3-methoxybutyl propionate, 3-methyl-3-methoxybutyl butylate, ethyl acetate, propyl acetate, butyl acetate, methyl acetoacetate, ethyl acetoacetate, methyl 3-methoxypropionate, ethyl 3-methoxy propionate, 3-ethoxy propionate methyl and 3-ethoxy propionate ethyl. The aforementioned solvents may be used independently or as a mixture of two or more types. Furthermore, at least one type of high boiling point solvent such as benzylethyl ether, dihexyl ether, diethylene glycol monomethyl ether, diethylene glycol monoethyl ether, acetonylacetone, isoholon, caproic acid, capric acid, 1-octanol, 1-nonanol, benzyl alcohol, benzyl acetate, ethyl benzoate, diethyl oxalate, diethyl maleate, γ-butyrolactone, ethylene carbonate, propylene carbonate and phenylcellosolve acetate may be added to the aforementioned solvent.

Various additives may be added to the photoresist formulations to provide certain desirable characteristic of the photoresist such as, for example, acid diffusion control agents to retard acid from migrating into unexposed areas of the coating, surfactants to improve coating of substrates, adhesion promoters to improve adhesion of the coating to the substrate and sensitizers to improve the photosensitivity of the photoresist coating during photoexposure, and antifoaming agents and air release agents, as well as other materials well know in the coatings industry.

In other embodiments other methanofullerenes are added to provide various desired properties such as improved sensitivity to the actinic radiation or for improvements in line edge roughness. Examples of such methanofullerenes include:

wherein x, y and R are described about and R can include a carboxylic acid derivative which together with the —(CH$_2$CH$_2$—O)$_a$ provides for a carboxylic ester structure. The —(CH$_2$CH$_2$—O) group may be substituted with fluorine atoms. A can be from about 1 to about 10. An more specific example of a disclosed methanofullerene comprises the general formula:

The components of the compositions of the current disclosure are included in ranges as follows based on weight/weight: methanofullerenes from about 1% to about 65%, crosslinker from about 10% to about 80%, photoacid generator from about 0.5% to about 50%. The percent solids of the composition may range from about 0.001%-about 25%.

The photoresist compositions can be coated onto substrate such as a silicon wafer or a wafer coated with silicon dioxide, aluminium, aluminum oxide, copper, nickel, any of a number of semiconductor materials or nitrides or other substrates well known the semiconductor industry, or a substrate having thereon an organic film, such as, for example, a bottom layer anti-reflective film or the like. The photoresist compositions are applied by such processes as spin coating, curtain coating, slot coating, dip coating, roller coating, blade coating and the like. After coating, the solvent is removed to a level wherein the coating can be properly exposed. In some cases a residual of 5% solvent may remain in the coating while in other cases less than 1% is required. Drying can be accomplished by hot plate heating, convection heating, infrared heating and the like. The coating is imagewise exposed through a mark containing a desired pattern.

Radiation suitable for the described photoresist compositions include, for example, ultraviolet rays (UV), such as the bright line spectrum of a mercury lamp (254 nm), a KrF excimer laser (248 nm), and an ArF excimer laser (193 nm), extreme ultraviolet (EUV) such as 13.5 nm from plasma discharge and synchrotron light sources, beyond extreme ultraviolet (BEUV) such as 6.7 nm exposure, X-ray such as synchrotron radiation. Ion beam lithography and charged particle rays such as electron beams may also be used.

Following exposure, the exposed coated substrate may optionally be post exposure baked to enhance the reaction of the photoacid generator, such as, for example, heating from about 30 to about 200° C. for about 10 to about 600 seconds. This may be accomplished by hot plate heating, convection heating, infrared heating and the like. The heating may also be performed by a laser heating processes such as, for example, a CO$_2$ laser pulse heating for about 2 to about 5 milliseconds. Both heating processes may be combined in tandem.

A flood exposure process may be applied after the pattern exposure to aid in further cure. Results have indicated that flood exposure reduces or eliminates pattern collapse after development of the negative-tone resists as well as reduction in line edge roughness. For example, a 532 nm continuous wave laser exposes the previously exposed resist for 1-2 sec followed by wet development. The flood process may or may not be followed by a heating step.

The unexposed areas are next moved using a developer. Such developers include organic solvents as well as aqueous solution such as aqueous alkali solution. When an organic solvent is used to remove the unexposed areas generally the solvent is less aggressive than the solvent that was used in preparing the photoresist composition. Examples of aqueous alkali development solution include, for example, at least one type of alkaline compound such alkali metal hydroxides, ammonia water, alkylamines, alkanolamines, heterocyclicamines, tetraalkyl ammonium hydroxides, cholines, and 1,8-diazabicyclo[5.4.0]-7-undecan,1,5-diazabicyclo[4.3.0]-5-nonene at a concentration of about 1 to about 10% by weight, such as, for example, about 2 to about 5% by weight. Water-soluble organic solvents such as methanol and ethanol and surfactants may also be added in suitable amounts to the alkaline aqueous solution, depending on the desired development characteristics and process parameters.

After development a final baking step may be included to further enhance the curing of the now exposed and developed pattern. The heating process may be, for example, from about 30 to about 600° C. for about 10 to about 120 seconds and may be accomplished by hot plate heating, convection heating, infrared heating and the like.

EXAMPLES

Synthesis Example A

Methanofullerene I:
[3-(4-t-butoxycarbonyl)phenyl-1-propyl malonate]-methano-[60]fullerene

Synthesis of 3-(4-t-butoxycarbonyl)phenyl-1-propanol (1)

To a 250 mL round bottom flask was added 3-(4-hydroxyphenyl)-1-propanol (10 g, 65.7 mmol), dichloromethane (75 mL) and di-tert-butyldicarbonate (14.36 g, 65.7 mmol). The mixture was stirred under nitrogen and cooled to 0° C. in an ice bath. Potassium carbonate (24.37 g, 176 mmol) and 18-crown-6 (0.90 g, 3.4 mmol) dissolved in dichloromethane were added. The resulting mixture was stirred and warmed to room temperature overnight. The crude reaction mixture was filtered through a silica gel and rinsed with ethyl acetate. The resulting solvent was evaporated and the residue was purified via flash column chromatography on silica gel with ethyl acetate:hexane (40%) as eluant. The third fraction was combined and the solvent removed to give 15.7 g (yield: 95%) of 1 as a yellow oil. The product was characterized by $^1$H NMR and MS.

Synthesis of 3-(4-t-butoxycarbonyl)phenyl-1-propyl malonate (2)

Dichloromethane (275 mL) was added to 1 (13.71 g, 54.4 mmol) in a 500 mL round bottom flask. To this was added, with stirring, pyridine (5.72 g, 72.35 mmol, 1.33 equiv) and the solution was cooled to 0° C. in an ice bath under nitrogen. Malonyl dichloride (2.65 mL, 27.2 mmol, in dichloromethane solution) was dropwise added. The initially clear solution became dark red upon complete addition of the malonyl dichloride. The mixture was stirred and warm up to room temperature overnight, upon which time it have become dark blue/green in color. The mixture was filtered through silica gel with ethyl acetate. The filtrate was evaporated and the residue was purified via flash column chromatography on silica gel using ethyl acetate as eluant. The fractions were collected and removed solvent to give 2 as yellow oil (9.56 g, 61% yield). The product was characterized by $^1$H and MS.

Synthesis of [3-(4-t-butoxycarbonyl)phenyl-1-propyl malonate]-methano-[60]fullerene(3)

In a round bottom flask, [60]fullerene(1 equivalent), 9,10-dimethylancethracene (22 equivalent) and toluene were added. The resulting solution was stirred under $N_2$ for one hour to completely dissolve the fullerene. Carbon tetrabromide (22 equivalent) and 2 (22 equiv) were added to the solution. 1,8-Diazabicyclo[5.4.0]undec-7-ene (108 equivalent) was added dropwise and the resulting mixture was stirred at room temperature overnight and the initial purple solution had become a dark red color. The crude mixture was poured though silica gel with toluene to remove unreacted [60]fullerene, and then rinsed with dichloromethane:ethyl acetate:methanol (2:2:1) to remove the red/brown band containing the crude products. The solvents were evaporated and the resulting residue 3 (dark red/brown oil) was obtained and characterized by $^1$H NMR and MALDI MS. Major components in 3 is multi-adducts fullerenes (n=4 to 6).

Synthesis Example B

Methanofullerene II: (3-phenol-1-propyl malonate)-methano-[60]fullerene

4

Synthesis of (3-phenol-1-propyl malonate)-methano-[60]fullerene (4)

In a 50 mL round bottom flask, 3 was dissolved in dichloromethane (10 mL) and stirred under nitrogen. Triflic acid (0.1 mol %) was added and stirred for 4 hours. The solvent was removed under vacuum and the resulting residue 4 was obtained and characterized by $^1$H NMR and MALDI MS.

Composition Example 1

Figure 1:
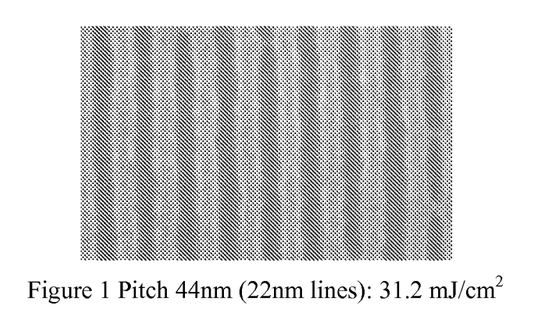
FIG. 1: shows an SEM showing the resolution obtained from example 1.

Into 100 mL of propylene glycol monomethyl ether (PGME) was added 0.25 g of methanofullerene I, 0.50 g of poly[(o-cresyl glycidyl ether)-co-formaldehyde] and 0.25 g of triphenylsulfonium hexafluoroantimonate and stirred for 1 hr at room temperature. The composition was applied to a silicon wafer and spin coated at 500 rpm for 5 sec followed by 2000 rpm for 60 sec. The coated wafer was then heated on a hot plate at 75° C. for 5 min to give a film of approximately 25 nm. The wafer was imagewise exposed to synchrotron based EUV light at 13-14 nm wavelength at 31.2 mJ/cm$^2$ and post exposure baked at 90° C. for 3 min. The unexposed areas were removed by puddle development in a 50:50 blend of monochlorobenzene and isopropyl alcohol for 20 sec followed by an isopropyl alcohol rinse. FIG. 1 shows the resulting 22 nm lines and spaces for example 1.

Composition Example 2

Figure 2:
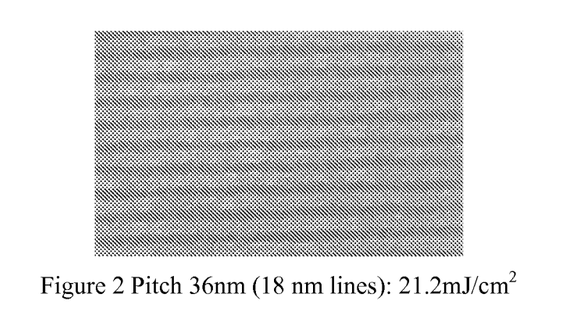
FIG. 2: shows an SEM showing the resolution obtained from example 2.

Example 1 was repeated but 150 mL of PGME was used to reduce the solids content. The resulting film thickness was 18 nm and the exposure was 21.2 mJ/cm$^2$. FIG. 2 shows the resulting 18 nm lines and spaces for example 2.

Composition Example 3

Figure 3:
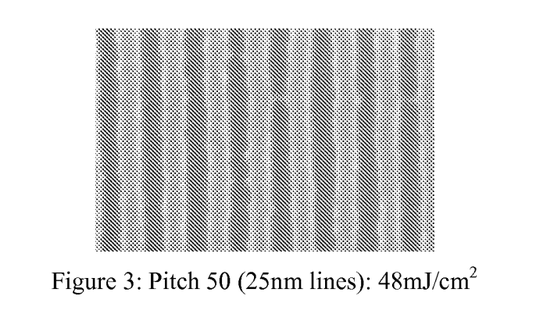
FIG. 3: shows an SEM showing the resolution obtained from example 3.

Example 1 was repeated using methanofullerene II in place of methanofullerene I. A 48 mJ/cm$^2$ exposure dosage was used. FIG. 3 shows the resulting 25 nm lines and spaces for example 3.

Composition Example 4

Figure 4:
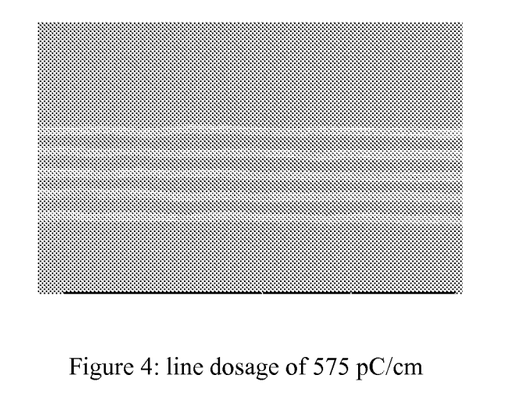
FIG. 4: shows an SEM showing the resolution obtained from example 4.

Example 1 was repeated using an E-beam exposure in place of 13-14 nm exposure. Area dose testing established a sensitivity of 90 μC/cm2 at 30 keV. For high resolution patterning a line dose of 575 pC/cm was applied at a nominal half-pitch of 50 nm, given lines of ~20 nm with ~30 nm spaces. FIG. 4 shows the resulting lines and spaces for example 4.

Composition Example 5

Figure 5:
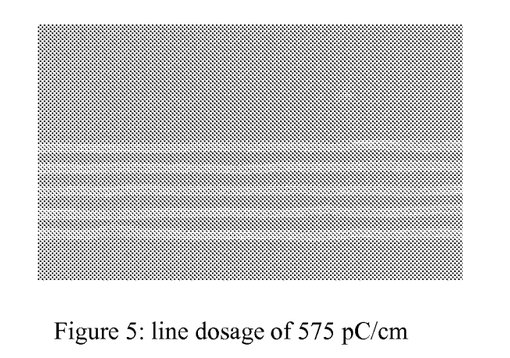
FIG. 5: shows an SEM showing the resolution obtained from example 5.

Example 3 was repeated using an E-beam exposure of 90 μC/cm$^2$ at 30 keV in place of 13-14 nm exposure. For high resolution patterning a line dose of 575 pC/cm was applied at a nominal half-pitch of 50 nm, given lines of ~20 nm with ~30 nm spaces FIG. 5 shows the resulting lines and spaces for the example 5.

Composition Example 6

Figure 6:
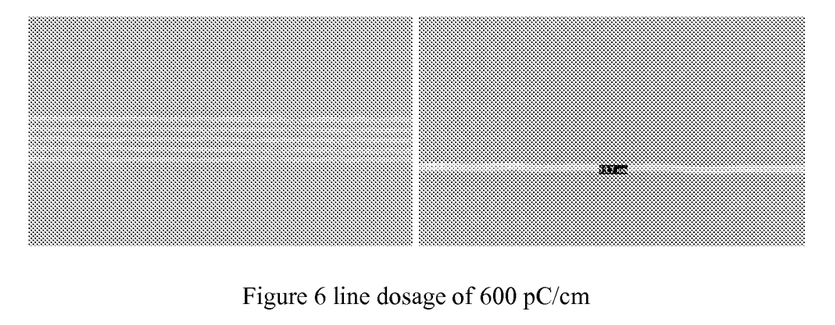
FIG. 6: shows an SEM showing the resolution obtained from example 6.

The formulation of Example 1 was repeated using 0.125 g of methanofullerene I and 0.125 g of a methanofullerene having tetraethylene glycol esters capped with acetic acid to provide acetate esters. The composition was applied to a silicon wafer and spin coated at 500 rpm for 5 sec followed by 2000 rpm for 60 sec. The coated wafer was then heated on a hot plate at 75° C. for 5 min to give a film of approximately 25 nm. The wafer was imagewise exposed to 40 μC/cm² of E-beam radiation and post exposure baked at 90° C. for 3 min. For high resolution patterning a line dose of 600 pC/cm was applied at a nominal half-pitch of 50 nm, given lines of ~20 nm with ~30 nm spaces The unexposed areas were removed by puddle development in a 50:50 blend of monochlorobenzene and isopropyl alcohol for 20 sec followed by an isopropyl alcohol rinse. FIG. 6 shows the resulting lines and spaces for example 6.

We claim:

1. A methanofullerene comprising the general formula:

wherein x is 10-48, y is 1-6, n is 0-1, alkyl is a branched or unbranched, substituted or unsubstituted divalent alkyl chain of 1-16 carbon atoms with or without one or more heteroatoms substituted into the chain, aryl is a substituted or unsubstituted divalent phenyl group, heteroaromatic group, or fused aromatic or fused heteroaromatic group, and at least one R is a photoacid labile group comprising —C=O—OR', wherein OR' is t-alkoxy, cycloketal, acetal, oxy-vinyl or t-butoxy.

2. The methanofullerene of claim 1, wherein the divalent alkyl chain comprises a methylene, ethylene or 1,3-propylene group.

3. The methanofullerene of claim 1, wherein at least one R is tert-butyl carbonate group.

4. The methanofullerene of claim 1, wherein the photoacid labile group is chosen from an alkoxycarbonyl group or a vinyl ether group.

5. A negative-tone photoresist composition comprising:
a. At least one methanofullerene comprising the general formula:

wherein x is 10-48, y is 1-6, n is 0-1, alkyl is a branched or unbranched, substituted or unsubstituted divalent alkyl chain of 1-16 carbon atoms with or without one or more heteroatoms substituted into the chain, aryl is a substituted or unsubstituted divalent phenyl group, heteroaromatic group, or fused aromatic or fused heteroaromatic group, and at least one R is a photoacid labile group comprising —C=O—OR', wherein OR' is t-alkoxy, cycloketal, acetal, oxy-vinyl or t-butoxy,
b. at least one photo acid generator,
c. at least one crosslinker, and
d. at least one solvent,
wherein the crosslinker crosslinks at least with the methanofullerene when processed.

6. The photoresist composition of claim 5, wherein the divalent alkyl comprises a methylene, ethylene or 1,3-propylene group.

7. The photoresist composition of claim 5, wherein at least one R is a tert-butyl carbonate group.

8. The photoresist composition of claim 5, wherein the photoacid labile group is an alkoxycarbonyl group or a vinyl ether group.

9. The photoresist composition of claim 5, wherein the at least one photoacid generator comprises an onium salt compounds, a sulfone imide compound, a halogen-containing compound, a sulfone compound, a sulfonate ester compound, a quinine-diazide compound, or a diazomethane compounds.

10. The photoresist composition of claim 9, wherein the at least one photoacid generator comprises a triphenylsulfonium salt.

11. The photoresist composition of claim 5, further comprising a novolac, a polyhydroxystyrene, a polyacrylate, or a maleic anhydride ester-acid polymer crosslinking additive.

12. The photoresist composition of claim 5, wherein the at least one crosslinker comprises an acid sensitive monomer or polymer.

13. The photoresist composition of claim 12, wherein the crosslinker comprises at least one of a glycidyl ether, glycidyl ester, glycidyl amine, a methoxymethyl group, an ethoxy methyl group, a butoxymethyl group, a benzyloxymethyl group, dimethylamino methyl group, diethylamino methyl group, a dibutoxymethyl group, a dimethylol amino methyl group, diethylol amino methyl group, a dibutylol amino methyl group, a morpholino methyl group, acetoxymethyl group, benzyloxy methyl group, formyl group, acetyl group, vinyl group or an isopropenyl group.

14. The photoresist composition of claim 12, wherein the crosslinker comprises one or more glycidyl ether groups attached to a novolac resin.

15. The photoresist composition of claim 5, wherein the solvent comprises esters, ethers, ether-esters, ketones, ketoesters, hydrocarbons, aromatics, and halogenated solvents.

16. The photoresist of claim 5, further comprising at least one methanofullerene comprising the general formula:

$$C_{2x}(>C—(COO—(CH_2CH_2—O)_a—R)_2)_y$$

wherein x is 10-48, y is 1-6, a is 1-10 and R is H or an acid labile group and wherein the —CH₂CH₂—O— may be optionally substituted with fluorine atoms.

17. A method of forming a patterned resist layer on a substrate comprising the steps of:
a. providing a substrate,
b. applying the photoresist compositions of claim 5, to a desired wet thickness,
c. heating the coated substrate to remove a majority of the solvent to obtain a desired thickness,
d. imagewise exposing the coating to actinic radiation,
e. removing the unexposed areas of the coating, and
f. optionally heating the remaining coating.

18. The method of claim 17, further comprising the step of heating the imagewise exposed coating prior to removing the unexposed areas of the coating.

19. The method of claim 17, wherein the unexposed areas are removed by treating with an organic solvent composition.

20. The method of claim 17, wherein the actinic radiation is ultraviolet or electron beam.

* * * * *